(12) United States Patent
D'Andrea et al.

(10) Patent No.: US 7,797,033 B2
(45) Date of Patent: Sep. 14, 2010

(54) METHOD OF USING, AND DETERMINING LOCATION OF, AN INGESTIBLE CAPSULE

(75) Inventors: David T. D'Andrea, Getzville, NY (US); John R. Semler, Williamsville, NY (US); Thomas H. White, Clarence, NY (US)

(73) Assignee: Smart Pill Corporation, Buffalo, NY (US)

( * ) Notice: Subject to any disclaimer, the term of this patent is extended or adjusted under 35 U.S.C. 154(b) by 1668 days.

(21) Appl. No.: 10/395,602

(22) Filed: Mar. 24, 2003

(65) Prior Publication Data

US 2003/0191430 A1 Oct. 9, 2003

Related U.S. Application Data

(60) Provisional application No. 60/370,540, filed on Apr. 8, 2002.

(51) Int. Cl.
    *A61B 5/05* (2006.01)
(52) U.S. Cl. ..................... 600/424
(58) Field of Classification Search ............... 600/424, 600/407, 301, 302, 160, 178
    See application file for complete search history.

(56) References Cited

U.S. PATENT DOCUMENTS

| 5,211,165 | A | | 5/1993 | Dumoulin et al. | |
|---|---|---|---|---|---|
| 5,279,607 | A | * | 1/1994 | Schentag et al. | 604/890.1 |
| 5,395,366 | A | * | 3/1995 | D'Andrea et al. | 604/890.1 |
| 5,429,132 | A | | 7/1995 | Guy et al. | |
| 5,604,531 | A | | 2/1997 | Iddan et al. | |
| 5,984,860 | A | * | 11/1999 | Shan | 600/116 |
| 6,632,216 | B2 | * | 10/2003 | Houzego et al. | 604/890.1 |
| 6,904,308 | B2 | | 6/2005 | Frisch et al. | |
| 6,929,636 | B1 | | 8/2005 | von Alten | |
| 6,939,290 | B2 | * | 9/2005 | Iddan | 600/109 |
| 6,951,536 | B2 | | 10/2005 | Yokoi et al. | |
| 2002/0099310 | A1 | | 7/2002 | Kimchy et al. | |
| 2002/0111544 | A1 | * | 8/2002 | Iddan | 600/310 |
| 2002/0198470 | A1 | * | 12/2002 | Imran et al. | 600/587 |
| 2003/0167000 | A1 | * | 9/2003 | Mullick et al. | 600/424 |
| 2003/0195415 | A1 | * | 10/2003 | Iddan | 600/424 |

FOREIGN PATENT DOCUMENTS

JP 07-111985 * 5/1995

* cited by examiner

*Primary Examiner*—Long V Le
*Assistant Examiner*—Jacqueline Cheng
(74) *Attorney, Agent, or Firm*—Phillips Lytle LLP

(57) ABSTRACT

The present invention broadly provides an improved ingestible capsule (28) that is arranged to sense one or more physiological parameters within a mammalian body, an to transmit such parameters to an extra-corporeal receiver (50). In use, the capsule and receiver perform the method of determining the real-time location of the capsule within a tract of a mammal. This method includes the steps of providing the capsule, the capsule having one or more sensors, ingesting the capsule, transmitting a signal from the capsule, receiving the transmitted signal, and determining the real-time location of the capsule within the tract as a function of the received signal. The received signal may also indicate the value of one or more sensed parameters.

33 Claims, 3 Drawing Sheets

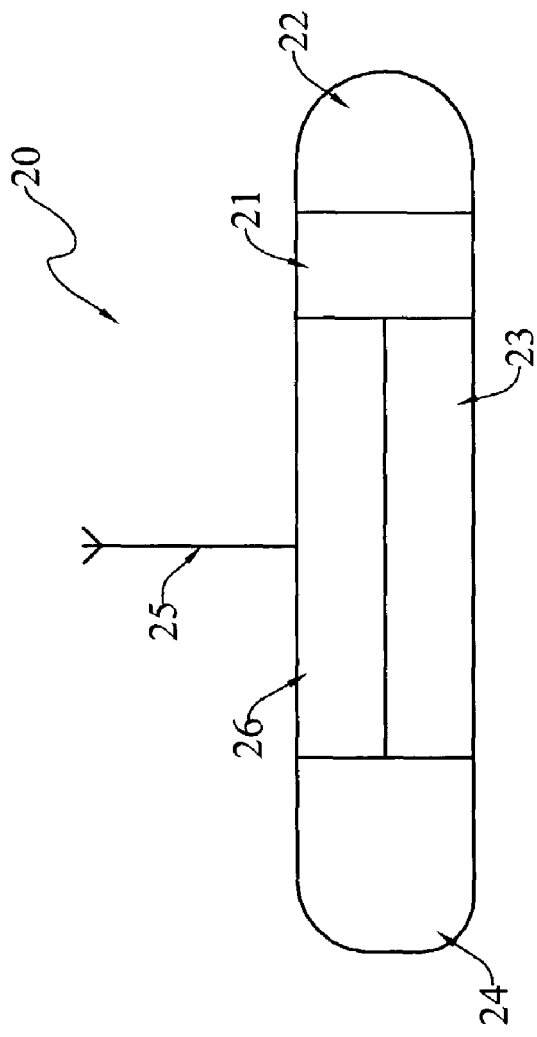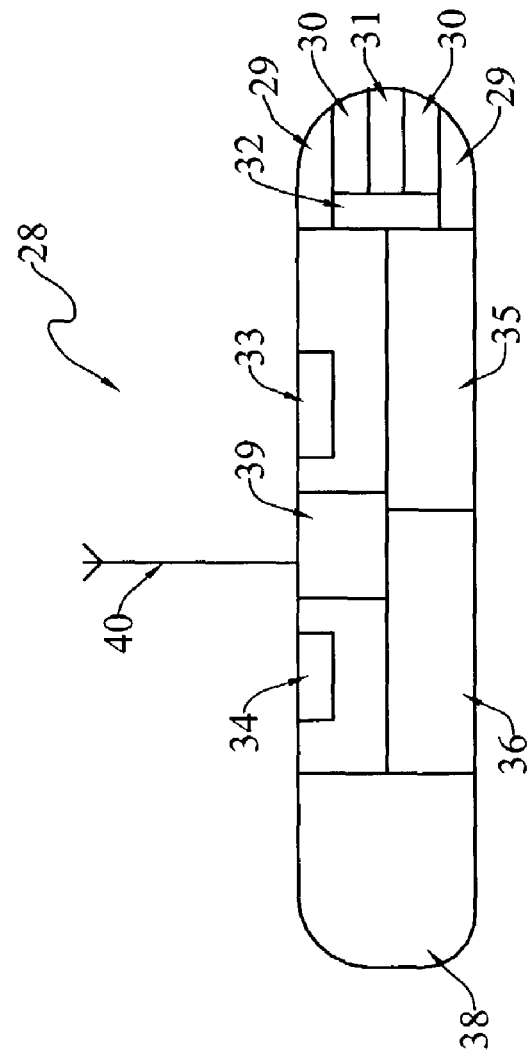
Fig. 1
Fig. 2

METHOD OF USING, AND DETERMINING LOCATION OF, AN INGESTIBLE CAPSULE

CROSS-REFERENCE TO RELATED APPLICATION

The present application claims the benefit of the earlier filing date of Provisional Patent Application Ser. No. 60/370,540, filed Apr. 8, 2002.

TECHNICAL FIELD

The present invention relates generally to the field of capsules that are adapted to be ingested, inserted, implanted or otherwise positioned in a mammalian body or tract to sense and determine one or more physiological parameters of the body or tract, and to communicate such sensed parameters via one or more tissue-penetrating signals to an extra-tract or extra-corporeal receiver.

BACKGROUND ART

The ever-advancing field of medical science continuously seeks new and improved diagnostic tools.

In early years, the diagnostic tools were largely represented by outward physical manifestations, such as blood pressure, temperature, chills, and the like. These manifestations were conditions and parameters that could be simply observed or measured from outside the body.

In more recent times, certain tools, such as endoscopes, have been developed that allow penetration of certain body tracts and cavities in an attempted to gather additional diagnostic data. For example, it is common today to use an endoscope-like device for a colonoscopy or sigmoidoscopy, to visually inspect the lower gastrointestinal tract. Endoscopes are also used to inspect other mammalian cavities. For example, in veterinary science, endoscopes are commonly used to inspect nasal cavities of horses and other animals.

There are a number of tracts in a mammalian body. These include the gastrointestinal tract, which extends from mouth to anus, the reproductive tract, the auditory tract, and the respiratory tract.

Considering a mammalian gastrointestinal tract for the moment, there is a large amount of physiological data that is potentially available within such tract. This data could include sensed parameters, such as pH, pressure, temperature, transit time, the presence or absence of a disease marker, the presence or absence of some other diagnostic marker, the presence or absence of an antibody or antigen, subsurface imaging, conductance, or even an electrical signal. In addition, it may be desirable to topically apply medicaments to a particular situs within such a tract, or, alternatively, to take a fluid sample at a selected location within such tract.

To this end, various radio telemetry capsules have been developed. Basically, these are small pill-like devices that can be ingested or swallowed by a patient. The capsule may have a sensor to determine a physiological parameter of the gastrointestinal tract. Some devices contemplate that the parameter be sensed and transmitted by an RF signal to an extra-corporeal antenna or receiver. For example, U.S. Pat. No. 3,739,279 appears to disclose an oscillator circuit for such an ingestible capsule. This patent then discloses a type of Colpitts oscillator which may be used in association with a telemetry sensor for determining physiological information within the patient's body. This patent recites that earlier telemetry systems have been developed for transmitting information such as temperature, pressure, specific ion activity, pH, pK and the like via an ingestible radio capsule.

Others have attempted to develop ingestible capsules that can be used to transmit a video signal to a location outside the body. References teaching this concept are shown and described in U.S. Pat. No. 6,240,312, B12 and in an internet article "Capsule Endoscopy Gets Map, Compass", http://www.gastroendonews.com/cgi-bin/wwread.pl?cat.=gastro&art=gen0802-01a.htm (Aug. 27, 2002). Still another reference is an article by Brad Lemly, "Ted Med", *Discover* (April 2003) [at pp. 70 et seq.]. This article even has a photograph of an ingestible video capsule manufactured by Given Imaging.

Other references for measuring temperature are provided in U.S. Pat. Nos. 4,844,076 and 4,689,621.

Other references have been directed toward dispensation of medicaments at selected sites within the gastrointestinal tract. See, e.g. U.S. Pat. Nos. 4,425,117, and 6,245,057.

Still another report on such ingestible capsules, appears in Milner, "Advances In and Prospects for Bio-Telemetry", symposium on Bio-Telemetry (Pretoria 1971).

Still another reference appears in an article by Alexandra Strikeman, "The Programmable Pill", *Technology Review* (M.I.T. May 22, 2001) [also available at http://www.technologyreview.com/magazine/may01/strikeman.asp].

Therefore, it is clear that others have attempted to develop ingestible pills or capsules for sensing and determining various physiological parameters, and broadcasting them via an RF signal to an extra-corporeal receiver.

However, the values of such sensed parameters may not be sufficient in and of themselves. Indeed, it is also important to know the location of the pill at the time the physiological parameter is sensed. To this end, U.S. Pat. No. 5,279,607 discloses an ingestible telemetry capsule with a means to determine location of the capsule. The '607 patent also discloses the capsule as having a medicament dispensing function. Thus, according to this patent, a capsule may be ingested to map the gastrointestinal tract. Thereafter, another capsule, this one containing a medicament, may be ingested. This capsule may be caused to dispense its medicament at a desired location within the body.

U.S. Pat. No. 5,395,366, discloses a concept related to the '607 patent. However, according to this device, a fluid sample may be taken into a compartment in an ingestible capsule at a selected location within the body.

While these devices, taken individually and collectively, show the state of, and advances in, the art, it is believed that it is now possible to determine the current or real-time location of a capsule within a tract in a mammalian body. It is also believed that this improved location-sensing method, may be used together with corroborative data provided by the sensors themselves to verify the location within the body.

DISCLOSURE OF THE INVENTION

With parenthetical reference to the corresponding parts, portions or surfaces of the disclosed embodiments, merely for purposes of illustration and not by way of limitation, the present invention broadly provides an improved method of using, and determining the real-time location of, an capsule that is adapted to be ingested, inserted, implanted or otherwise positioned within a mammalian body or tract.

As used herein, the expression "real-time location" means the location of the capsule at the time a signal is transmitted from the capsule to an extra-tract or extra-corporeal receiver, regardless of whether the signal is read contemporaneously when received, or recorded and stored for subsequent reading or analysis.

In one aspect, the invention provides an improved method of determining the real-time location of a capsule (28) in a tract of a mammal, comprising the steps of: providing a capsule, the capsule having sensors (29, 30, 31, 33, 34) to determine at least two physiological parameters of the tract, the capsule also having a transmitter (39) operatively arranged to transmit a signal reflecting such sensed parameters; inserting the capsule into the tract; transmitting the signal from the transmitter; receiving the transmitted signal exteriorly (at 41) of the tract; and determining the real-time location of the capsule within the tract as a function of the received signal.

In another aspect, the invention provides an improved method of determining the real-time location of a capsule in a tract of a mammal, comprising the steps of: providing a capsule, the capsule having at least one sensor operatively arranged to determine a physiological parameter of the tract, the capsule also having a transmitter; inserting the capsule into the tract; transmitting from the transmitter a signal reflective of the value the sensed parameter; receiving the transmitted signal exteriorly of the tract; and determining the real-time location of the capsule within the tract as a function of the received signal and the received value of the sensed parameter.

In another aspect, the invention provides an improved method of determining the value of a physiological parameter in a tract of a mammal, comprising the steps of: providing an MRI-compatible capsule, the capsule having a sensor operatively arranged to determine at least one physiological parameter of the tract, the capsule also having a transmitter operatively arranged to transmit a signal reflecting such sensed parameter; inserting the capsule into the tract; tethering the capsule to an object; transmitting the signal from the transmitter; receiving the transmitted signal exteriorly of the tract; and determining the value of the sensed parameter as a function of the received signal.

In the foregoing methods, the signal may be a radio signal and/or an acoustic signal. The tract may be an auditory, respiratory, reproductive and a gastrointestinal tract. The capsule may be inserted or ingested into the gastrointestinal tract. The location of the capsule may be determined as a function of the phase difference between the transmitted and received signals, or as a function of the difference in time between the time of transmission of the transmitted signal and the time of receipt of the received signal. The method may include the additional step of determining the value of at least one of the sensed parameters exteriorly of the tract as a function of the received signal.

Alternatively, the real-time location of the capsule within the tract may be determined as a function of the strength of the received signal and such received value of at least one of the sensed parameters.

The capsule may be tethered to an object, such as another capsule that is inserted into the tract, or to an object located outside the body.

The capsule may have a storage compartment containing medicament, and the method may include the additional step of dispensing medicament from the compartment at a desired location within the tract. Alternatively, the capsule may have a fluid storage compartment, and the method may include the additional step of taking in a fluid sample to the compartment at a desired location within the tract. At least one of the sensors may be arranged within the fluid storage compartment.

In one form, the capsule may have sensors to determine at least two of the physiological parameters, wherein some of the sensed parameters are used to determine a first location of the capsule, wherein others of the sensed parameters are used to determine a second location of the capsule, and wherein the first and second locations are compared to corroborate the location of the capsule.

The sensed physiological parameters may be selected from the group consisting of: pH, pressure, temperature, transit time, a disease marker, a diagnostic marker, an antibody, an antigen, subsurface imaging (e.g., fluorescence or optical imaging), conductance, and an electrical signal.

In another aspect, the invention provides an improved method of determining the real-time location of a capsule in a tract of a mammal, comprising the steps of: providing a capsule, the capsule also having a transmitter operatively arranged to transmit an RF signal, either continuously or intermittently, at a frequency in excess of about 5 kilohertz; inserting the capsule into the tract; transmitting the signal from the transmitter; receiving the transmitted signal exteriorly of the tract; and determining the real-time location of the capsule within the tract as a function of the received signal. In this aspect, the transmitter may be operatively arranged to transmit a signal a frequency of less that about 10 gigahertz.

In another aspect, the invention provides an improved method of determining the real-time location of a capsule in a tract of a mammal, comprising the steps of: providing a capsule, the capsule also having a transmitter operatively arranged to transmit an acoustic signal at a frequency in excess of about 100 hertz; inserting the capsule into the tract; transmitting the signal from the transmitter; receiving the transmitted signal exteriorly of the tract; and determining the real-time location of the capsule within the tract as a function of the received signal. In this aspect, the transmitter may be operatively arranged to transmit a signal, either continuously or intermittently, a frequency of less that about 1.5 megahertz.

In another aspect, the invention provides an improved method of determining the real-time location of a capsule in a tract of a mammal, comprising the steps of: providing a capsule, the capsule having a transmitter operatively arranged to transmit a signal; inserting the capsule into the tract; providing a plurality of receivers exteriorly of the tract; transmitting the signal from the transmitter; receiving the transmitted signal on the receivers; and determining the real-time location of the capsule as a function of the signals received by the receivers. The capsule may have at least one sensor operatively arranged to determine at least one physiological parameter within the tract, and the transmitter may be arranged to generate a signal reflective of such sensed parameter. The real-time location of the capsule may be determined using algorithm-based logic, such as artificial intelligence, a neural net, or a determinative statistical approach.

In still another aspect, the invention provides an improved method of determining the value of a parameter in a mammal body, comprising the steps of: providing a capsule, the capsule having a sensor to determine a physiological parameter of the body and having a transmitter operatively arranged to transmit a signal; inserting the capsule into the body; providing a receiver exteriorly of the body; transmitting the signal from the transmitter; receiving the transmitted signal on the receiver; and determining the value of the physiological parameter exteriorly of the body as a function of the signals received by the receiver. In this aspect, the capsule may be stationary within the body.

Accordingly, the general object is to provide an improved method of determining the real-time location of a capsule within a tract of a mammalian body.

Another object is to provide a method of determining at least one physiological parameter within a mammalian body and the real-time location of the place from which that parameter was taken.

These and other objects and advantages will become apparent from the foregoing and ongoing written specification, the drawings and the appended claims.

BRIEF DESCRIPTION OF THE DRAWINGS

FIG. 1 is a schematic view of a single-sensor capsule.

FIG. 2 is a schematic view of a multi-sensor capsule.

DESCRIPTION OF THE PREFERRED EMBODIMENTS

Figure 3:
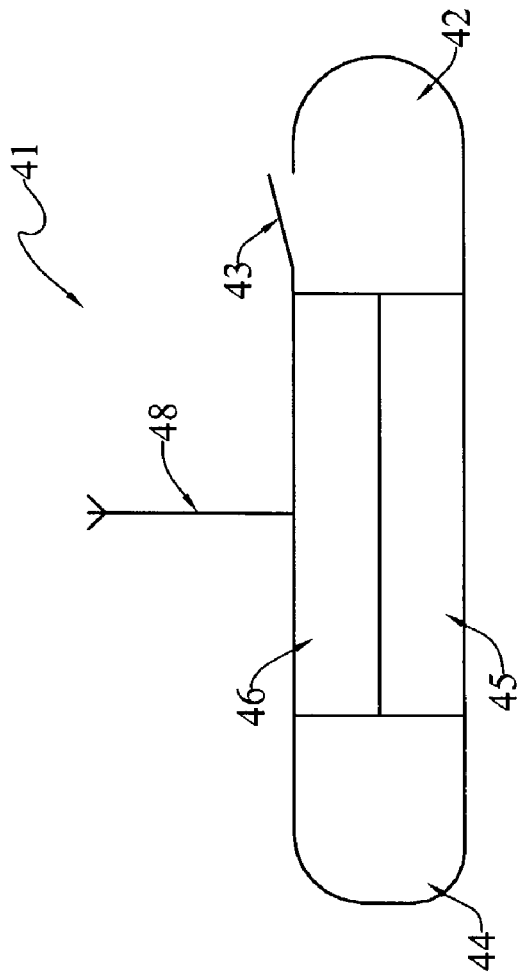
FIG. 3 is a schematic view of a medicament-dispensing capsule.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, and more particularly to FIG. 1 thereof, an improved single-sensor ingestible capsule is generally indicated at 20. Capsule 20 is shown as being an elongated ellipsoid-shaped device, somewhat resembling a medicament capsule. The enclosed drawing is not to scale, but, rather, is schematic. Sensor 20 is shown as broadly including a pressure sensor 21, a non-clogging pressure port 22, a compartment containing transmitting electronics 23, a battery compartment 24, a transmitting antenna, schematically indicated at 25, and a power switch and seal, generally indicated at 26. In the schematic view of FIG. 1, antenna 25 is shown as extending upwardly and away from the body of the capsule. However, this is only for schematic purposes. In reality, the antenna would be contained wholly within the capsule.

Capsule 20 is adapted to be ingested, implanted, inserted or otherwise positioned within a mammalian body or tract, to sense pressure within the body or tract, and to transmit such sensed pressure in the form of an RF or acoustic signal via antenna 25.

FIG. 2 shows a variant form of capsule that has multiple sensors. This capsule, generally indicated at 28, is schematically shown as having one or more surface pressure sensors 29, an optical ultraviolet light source channel 30, an optical detector, scanner and lens combination, indicated at 31, a compartment 32 containing optical scanning electronics, a temperature sensor 33, a pH sensor 34, a compartment 35 containing a microprocessor, a compartment 36 containing sensor signal conditioning electronics, a battery compartment 38, a compartment containing transmitter electronics 39, and an antenna 40 which is arranged to broadcast an RF or acoustic signal reflecting the values of such sensed parameters. Here again, antenna 40 is depicted schematically.

FIG. 3 is a schematic view of a medicament dispensing capsule, generally indicated at 41. Capsule 41 is shown as including a compartment 42 containing a medicament or fluid and closed by a door 43, a battery compartment 44, a receiver, and a power switch and seal compartment 46, and a receiving antenna 48 that is arrange to receive an RF or acoustic signal broadcast from outside the body or tract and to cause the medicament to be dispensed at a desired location within the body or tract.

Figure 4:
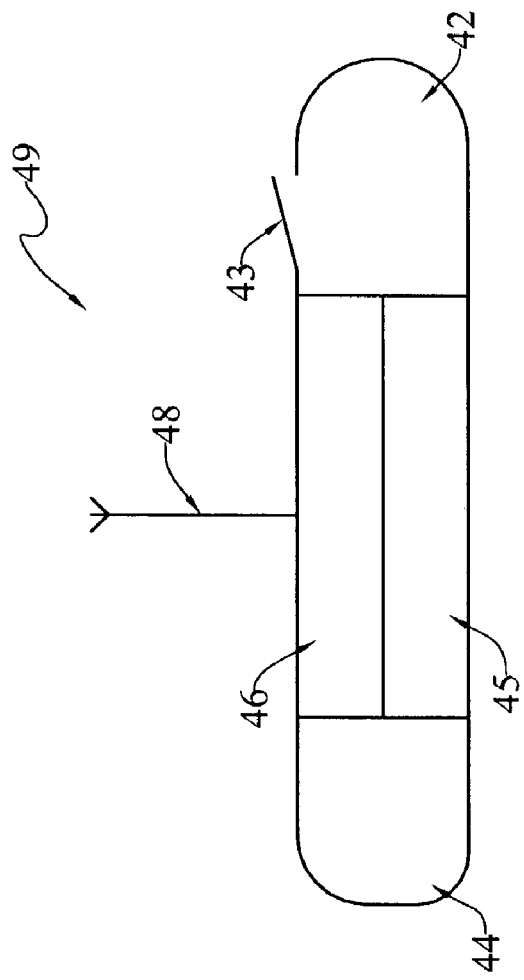
FIG. 4 is a schematic view of a fluid-sampling capsule.

FIG. 4 is a schematic view of a fluid sampling, generally indicated at 49. Capsule 41 is again shown as including a compartment 42 into which a fluid sample may be received and closed by a door 43, a battery compartment 44, a receiver, and a power switch and seal compartment 46, and a receiving antenna 48 that is arrange to receive an RF or acoustic signal broadcast from outside the body or tract and to cause the medicament to be dispensed at a desired location within the body or tract.

Figure 5:
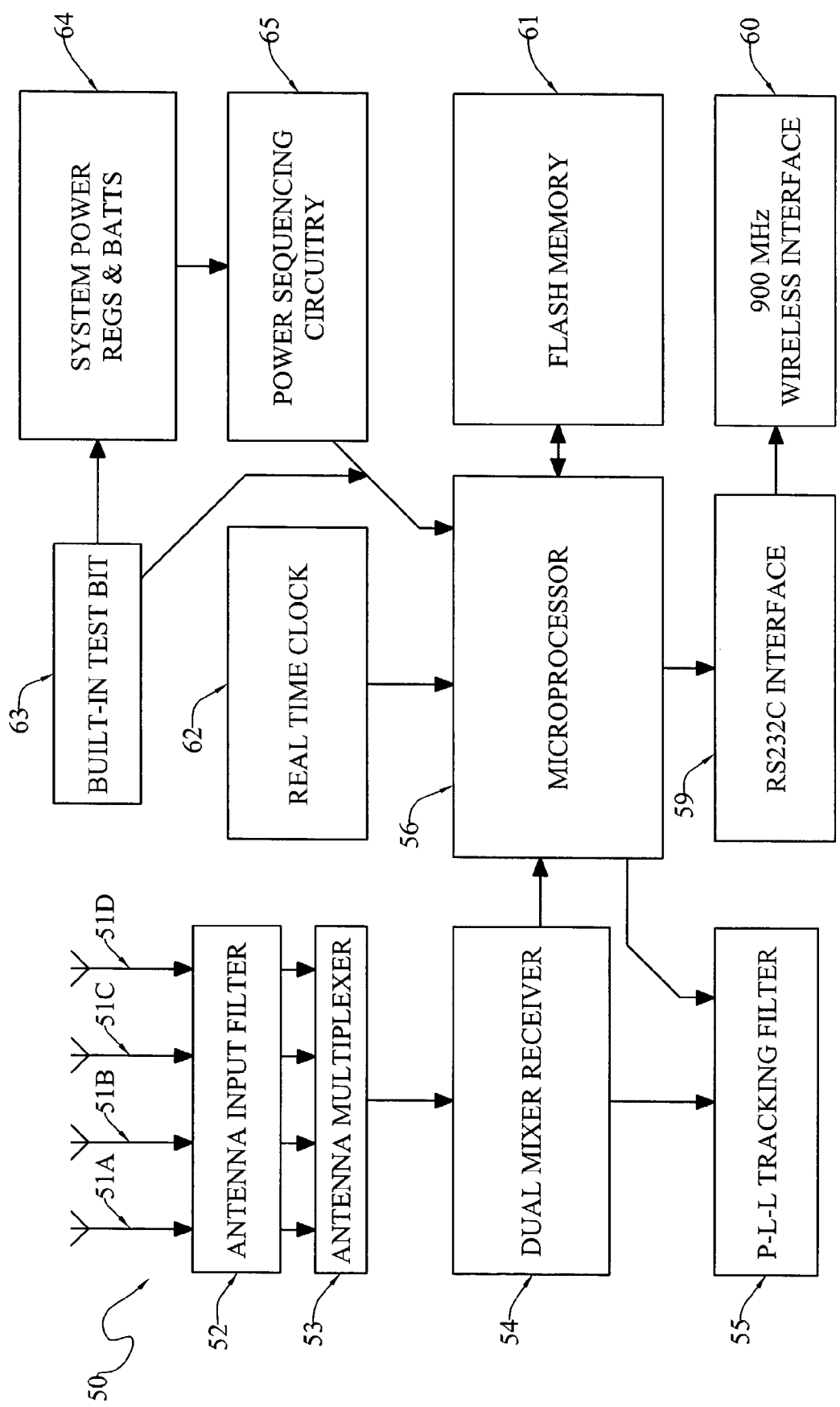
FIG. 5 is a schematic view of the receiving circuitry for the capsule shown in FIGS. 1 and/or 2.

FIG. 5 is a schematic view of the receiving apparatus. Basically, the apparatus, generally indicated at 50, contains a plurality of receiving antennas, severally indicated at 51 and individually identified by the letters A, B, C and D, an antenna input filter 52, an antenna multiplexer 53, and a dual mixer receiver 54. The output of receiver 54 is provided to a phase-locked-loop filter 55, and to a microprocessor 56. Filter 55 and microprocessor 56 are coupled directly via line 58. The output of microprocessor 56 is provided to an RS 232C interface, represented by block 59, and then to a 900 MHz wireless interface, represented by block 60. The output of microprocessor 56 is also provided to a flash memory device, represented by block 61. A real-time clock, represented by block 62, is arranged to provide a signal to microprocessor 56. A built-in test unit, represented by block 63, is connected to system power regulators and RF components, communication subsystems and batteries, represented by box 64. Power sequencing circuitry, contained within box 65, is connected to the regulators and batteries, and is also supplies a signal to the microprocessor via conductor 66. The test unit 63 is connected to the conductor 66 communicating the power sequencing circuitry with the microprocessor.

The invention broadly provides an improved method of determining the real-time location of the capsule in a mammalian body or tract. The capsule may be inserted, ingested, implanted or otherwise positioned into the tract. The tract may be a gastrointestinal tract, an auditory tract, a respiratory tract, or a reproductive tract. The capsule is arranged to broadcast a radio and/or acoustic signal reflecting the values of one or more physiological parameters sensed by the capsule, as indicated above. For example, the patient will swallow a capsule. As the capsule is advanced along the gastrointestinal tract, the capsule will broadcast a signal reflective of the parameters sensed along its passage. These parameters may be sensed continuously or intermittently, as desired. Indeed, the parameters may be sensed and determined on an analog or digital basis. The capsule then transmits an RF or acoustic signal. The signal is received by the receiving antennas. The receive signal is then used to determine the real-time location of the capsule at the time the signal was sent. This does not necessarily mean that the value of the sensed parameter must be read or interpreted at the time of receipt. Rather, it could be stored for reading or analysis at some later time.

Nevertheless, by determining the real-time location of the capsule, the electronics determine the precise location from which the signal was sent. The location may be determined in a number of ways. For example, the signal may be used to determine the spatial location of the capsule within the body chest barrel. For example, this could be determined in terms in terms of the x, y and z coordinates of the capsule location.

Alternatively, or in addition thereto, the location could be determined in terms of the position of the capsule within the gastrointestinal tract (i.e., whether in the stomach, the small intestine, the large intestine, or the like). These various portions of the gastrointestinal tract are believed to have various indicating parameters. For example, the pH of the stomach may be relatively acidic. On the other hand, the pressure within the small intestine may be the dominant parameter. Hence, by sensing a change in the pH and an increase in the pressure, one might infer that the capsule has passed from the stomach into the small intestine. Thus, the capsule may be used to measure motility of the capsule as it progresses through the patient's body. Knowing the location of the capsule within the gastrointestinal tract when one reading is transmitted, monitoring the progress of same, and knowing the location of the capsule when a subsequent reading is transmitted, one can calculate the speed of propagation or time of transit of the capsule through the particular section of the tract.

The location of the capsule may be determined either as a function of the phase difference between the transmitted and received signals, as a function of the difference in the time between the time of transmission of the transmitted signal and the time of receipt of the received signal, or as a function of differences of signal amplitude received at different receivers. In addition, the capsule may be tethered to some object. For example, the capsule could be tethered to another capsule that is ingested or otherwise inserted into the body tract, or to some object located outside of the tract, or at least the portion of the tract under consideration. The capsule may be operatively arranged to dispense medicament at a desired location, such as shown and described in U.S. Pat. No. 5,279,607, or may be used to take in a fluid sample at a desired location of the body, such as shown and described in U.S. Pat. No. 5,395,366.

In one particular unique form, the capsule has multiple sensors to determine at least three physiological parameters, such as pH, pressure, temperature, transit time, the presence or absence of a disease marker, the presence or absence of a diagnostic marker, an antibody, an antigen, subsurface imaging, conductance and/or an electrical signal. Some of these sense parameters may be used to determine a first location and others of the parameters are used to determine a second location of the capsule. The first and second locations may be compared to corroborate the apparent location of the capsule.

Thus, the real-time location of the capsule may be determined as the function of the received signal and a receive value of the sensed parameter.

Preferably, the capsule is MRI-compatible such that its location within the body can also be determined by means of magnetic residence imaging, if desired.

In one form, the capsule may have a fluid storage compartment, and the improved method may include the additional step of dispensing fluid from the compartment into a portion of the tract, and measuring the volume of the compartment of such portion as a function of the concentration of the dispensed fluid with the portion. This is particularly useful in determining the conformance or capacity of a stomach.

If the transmitter is an RF signal, it is presently preferred that the transmitter broadcast the signal at a frequency in excess of about 5 kilohertz, but less than about 10 gigahertz. If the transmitted medium is an acoustic wave, it is desired that the frequence by in excess of 100 Hz, but less than about 1.5 MHz.

The invention is not limited to use within a tract of a mammalian body. Indeed, the capsule could be implanted or otherwise positioned in a particular organ or cavity of the body, and used to transmit a signal reflecting the value of a sensed parameter from a stationary location.

If the inventive capsule is used in a gastrointestinal tract, the location of the capsule is preferably determined electronically by means of algorithm-based logic, such as artificial intelligence, a neural net, or a deterministic statistics approach.

Therefore, while several forms of the improved capsule and receiver have been shown and described, and various changes and modifications to the apparatus and method discussed, persons skilled in this art will readily appreciate that various additional changes and modifications may be made without departing from the spirit of the invention, as defined and differentiated by the following claims.

What is claimed is:

1. A method of determining the real-time location of a capsule in a tract of a mammal, comprising the steps of:
providing a capsule, said capsule having sensors to determine at least a first physiological parameters of said tract and a second physiological parameter of said tract that is different from said first physiological parameter, said capsule also having a transmitter operatively arranged to transmit a signal reflecting such sensed parameters;
inserting said capsule into said tract;
transmitting a first said signal from said transmitter;
receiving said first transmitted signal exteriorly of said tract;
determining the value of said first sensed parameters;
determining the phase or amplitude of said first signal;
determining a first location of said capsule within said tract as a function of both (i) said determined phase or amplitude of said received signal and (ii) said determined value of said first sensed parameter;
transmitting a second said signal from said transmitter;
receiving said second transmitted signal exterior of said tract;
determining the value of said second sensed parameter;
determining the phase or amplitude of said second signal; and
determining a second location of said capsule within said tract as a function of both (i) said determined phase or amplitude of said received signal and (ii) said determined value of said second sensed parameter.

2. The method as set forth in claim 1 wherein said signal is a radio signal and/or an acoustic signal.

3. The method as set forth in claim 1 wherein said tract is one of an auditory, respiratory, reproductive, and gastrointestinal tract.

4. The method as set forth in claim 3 wherein said tract is said gastrointestinal tract, and wherein capsule is ingested into said gastrointestinal tract.

5. The method as set forth in claim 1 wherein said step of determining the phase or amplitude of said signal comprises determining either the phase difference between the transmitted and received signals, the difference in time between the time of transmission of said transmitted signal and the time of receipt of said received signal, or the difference in signal amplitude received at multiple locations.

6. The method as set forth in claim 1 wherein the value of at least one of said sensed parameters is determined exteriorly of said tract.

7. The method as set forth in claim 1 wherein said capsule has a storage compartment containing medicament, and further comprising the additional step of dispensing medicament from said compartment at a desired location within said tract.

8. The method as set forth in claim 1 wherein said capsule has a fluid storage compartment, and further comprising the additional step of taking in a fluid sample to said compartment at a desired location within said tract.

9. The method as set forth in claim 8 wherein at least one of said sensors is arranged within said fluid storage compartment.

10. The method as set forth in claim 1 wherein said first and second locations are compared to corroborate the location of said capsule.

11. The method as set forth in claim 1 wherein said first and second physiological parameters are selected from the group consisting of pH, pressure, temperature, transit time, a disease marker, a diagnostic marker, an antibody, an antigen, subsurface imaging, conductance, and an electrical signal.

12. A method of determining the real-time location of a capsule in a tract of a mammal, comprising the steps of:
providing a capsule, said capsule having at least a first sensor operatively arranged to determine a first physiological parameter of said tract and a second sensor operatively arranged to determine a second physiological parameter of said tract that is different from said first physiological parameter, said capsule also having a transmitter;
inserting said capsule into said tract;
transmitting from said transmitter a first signal;
receiving said first transmitted signal exteriorly of said tract;
determining the value of said first sensed physiological parameter of said tract;
determining the phase or amplitude of said first signal;
determining the location of said capsule within said tract as a function of both (i) said determined phase or amplitude of said first received signal and (ii) said determined value of said first sensed parameter;
transmitting from said transmitter a second signal;
receiving said second transmitted signal exterior of said tract;
determining the value of said second sensed parameter;
determining the phase or amplitude of said second signal; and
determining a second location of said capsule within said tract as a function of both (i) said determined phase or amplitude of said received second signal and (ii) said determined value of said second sensed parameter.

13. The method as set forth in claim 12 wherein said signal is a radio signal and/or an acoustic signal.

14. The method as set forth in claim 12 wherein said tract is one of an auditory, respiratory, reproductive and a gastrointestinal tract.

15. The method as set forth in claim 14 wherein said tract is said gastrointestinal tract, and wherein said capsule is ingested into said gastrointestinal tract.

16. The method as set forth in claim 12 wherein said step of determining the phase or amplitude of said signal comprises determining either the phase difference between the transmitted and received signals, the difference in time between the time of transmission of said transmitted signal and the time of receipt of said received signal, or the difference in amplitude of received signals from multiple receivers.

17. The method as set forth in claim 12 wherein the value of said sensed parameter is determined exteriorly of said tract.

18. The method as set forth in claim 12 wherein said capsule has a storage compartment containing medicament, and further comprising the additional step of dispensing medicament from said compartment at a desired location within said tract.

19. The method as set forth in claim 12 wherein said capsule has a fluid storage compartment, and further comprising the additional step of taking in a fluid sample to said compartment at a desired location within said tract.

20. The method as set forth in claim 19 wherein at least one of said sensors is arranged within said fluid storage compartment.

21. The method as set forth in claim 12 wherein said first and second locations are compared to corroborate the location of said capsule.

22. The method as set forth in claim 12 wherein said first and said second physiological parameters are selected from the group consisting of pH, pressure, temperature, transit time, a disease marker, a diagnostic marker, an antibody, an antigen, subsurface imaging, conductance, and an electrical signal.

23. A method of determining the value of a physiological parameter in a tract of a mammal, comprising the steps of:
providing an MRI-compatible capsule, said capsule having a first sensor operatively arranged to determine a first physiological parameter of said tract and a second sensor operatively arranged to determine a second physiological parameter of said tract that is different from said first physiological parameter, said capsule also having a transmitter operatively arranged to transmit a signal reflecting such sensed parameters;
inserting said capsule into said tract;
transmitting a first said signal from said transmitter;
receiving said first transmitted signal exteriorly of said tract;
determining the value of said first sensed parameter;
determining the phase or amplitude of said first signal; and
determining the location of said capsule within said tract as a function of both (i) said determined phase or amplitude of said first received signal and (ii) said determined value of said first sensed parameter;
transmitting a second said signal from said transmitter;
receiving said second transmitted signal exterior of said tract;
determining the value of said second sensed parameter;
determining the phase or amplitude of said second signal; and
determining a second location of said capsule within said tract as a function of both (i) said determined phase or amplitude of said received second signal and (ii) said determined value of said second sensed parameter.

24. The method as set forth in claim 23 wherein said signal is a radio signal and/or an acoustic signal.

25. The method as set forth in claim 23 wherein said tract is one of an auditory, respiratory, reproductive and a gastrointestinal tract.

26. The method as set forth in claim 25 wherein said tract is said gastrointestinal tract, and wherein said capsule is ingested into said gastrointestinal tract.

27. The method as set forth in claim 23 wherein said step of determining the phase or amplitude of said signal comprises determining the phase difference between the transmitted and received signals, the difference in time between the time of transmission of said transmitted signal and the time of receipt of said received signal, or the difference in amplitude of received signals from multiple receivers.

28. The method as set forth in claim 23 wherein the value of at least one of said sensed parameters is determined exteriorly of said tract.

29. The method as set forth in claim 23 wherein said capsule has a storage compartment containing medicament, and further comprising the additional step of dispensing medicament from said compartment at a desired location within said tract.

30. The method as set forth in claim 23 wherein said capsule has a fluid storage compartment, and further comprising the additional step of taking in a fluid sample to said compartment at a desired location within said tract.

31. The method as set forth in claim 30 wherein at least one of said sensors is arranged within said fluid storage compartment.

32. The method as set forth in claim 23 wherein said first and second locations are compared to corroborate the location of said capsule.

33. The method as set forth in claim 23 wherein said first and said second of said physiological parameters are selected from the group consisting of pH, pressure, temperature, transit time, a disease marker, a diagnostic marker, an antibody, an antigen, subsurface imaging, conductance, and an electrical signal.

* * * * *